_United States Patent_ [19]

Walker et al.

[11] Patent Number: 4,994,047
[45] Date of Patent: Feb. 19, 1991

[54] MULTI-LAYER CANNULA STRUCTURE

[75] Inventors: Jack M. Walker, Portola Valley; Joseph R. Thomas, Fremont, both of Calif.

[73] Assignee: Menlo Care, Inc., Palo Alto, Calif.

[21] Appl. No.: 191,007

[22] Filed: May 6, 1988

[51] Int. Cl.$^5$ .............................................. A61M 5/00
[52] U.S. Cl. .................... 604/264; 604/265; 604/280; 128/768
[58] Field of Search ................ 604/21, 27, 48, 54, 604/96, 264–266, 270, 275, 280, 282

[56] References Cited

U.S. PATENT DOCUMENTS

| | | | |
|---|---|---|---|
| 3,566,874 | 3/1971 | Shepherd et al. | 604/265 |
| 3,598,126 | 8/1971 | Hoeltzenbein | 604/282 |
| 3,861,396 | 1/1975 | Vaillancourt et al. | 604/265 |
| 4,202,880 | 5/1980 | Fildes et al. | 424/78 |
| 4,424,305 | 1/1984 | Gould et al. | 528/75 |
| 4,459,318 | 7/1984 | Hyans | 604/265 |
| 4,527,293 | 7/1985 | Eckstein et al. | 604/266 |
| 4,596,563 | 6/1986 | Pande | 604/264 |
| 4,668,221 | 5/1987 | Luther | 604/265 |
| 4,798,597 | 1/1989 | Vaillancourt | 604/265 |
| 4,846,812 | 7/1989 | Walker et al. | 604/264 |

_Primary Examiner_—John D. Yasko
_Assistant Examiner_—Anthony M. Gutowski
_Attorney, Agent, or Firm_—Fleisler, Dubb, Meyer & Lovejoy

[57] ABSTRACT

A swellable cannula is formed of concentric inner and outer hydrophilic and substantially non-hydrophilic layer structures. The hydrophilic layer structure comprises at least 2/3rds of the cross-sectional area of the wall of the cannula. The substantially non-hydrophilic layer structure is either substantially water impermeable or allows water to pass through at a controlled rate. The substantially non-hydrophilic layer structure may also control the diffusion of medicaments. The cannula has controlled softenability and swellability characteristics.

23 Claims, 2 Drawing Sheets

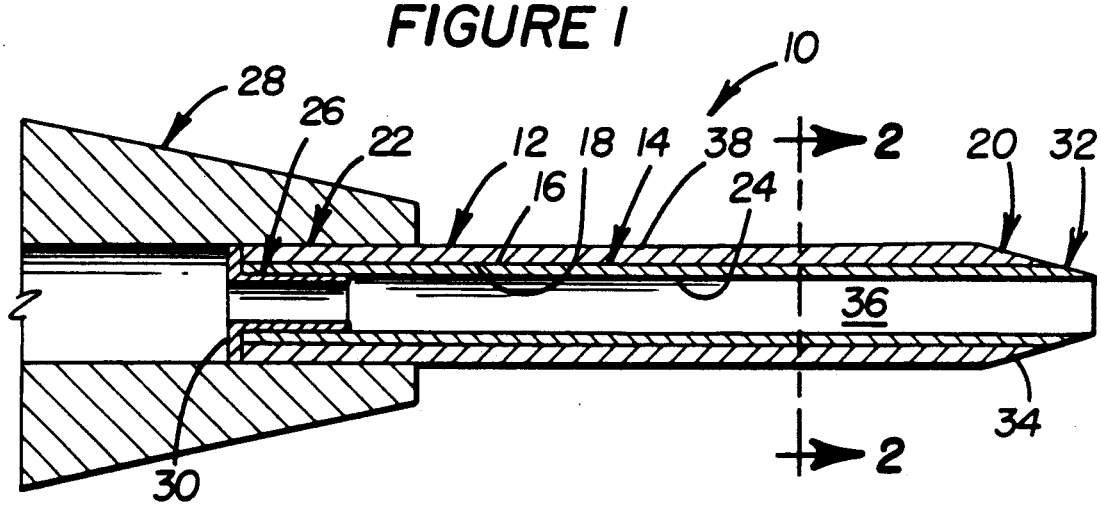
FIGURE 1
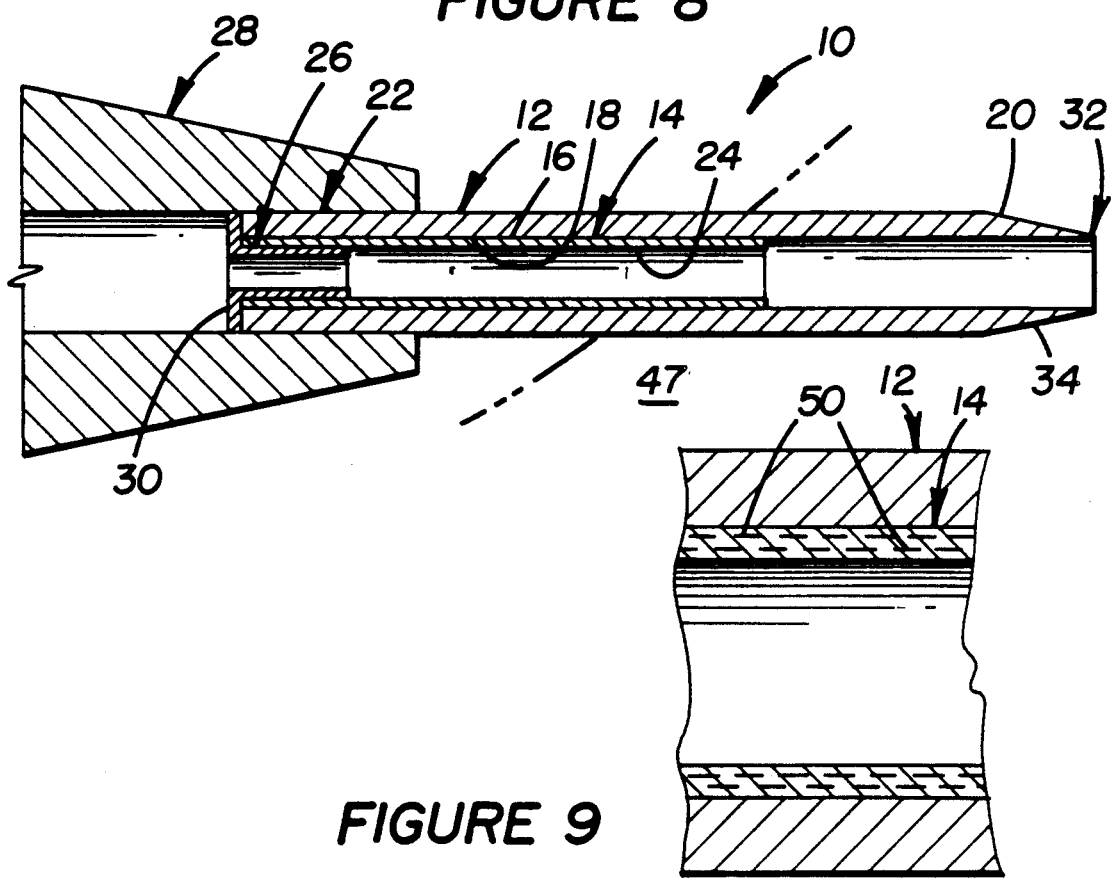
FIGURE 8
FIGURE 9

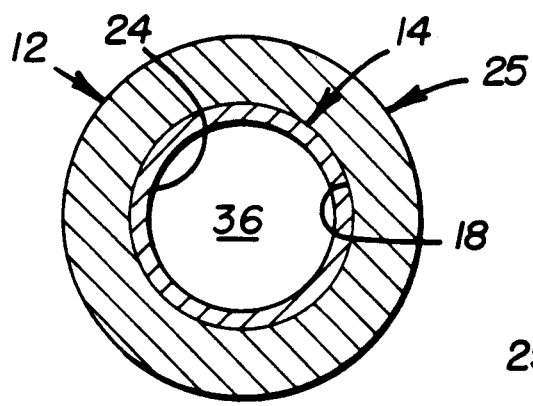
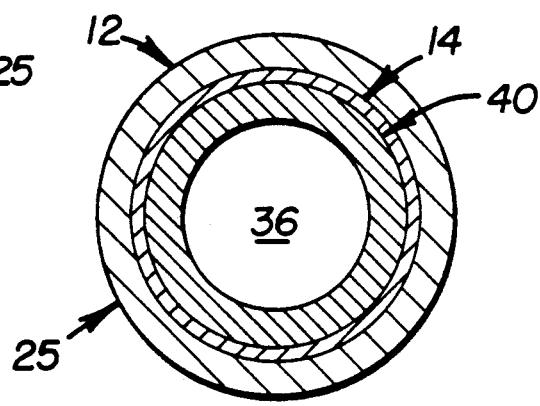
FIGURE 2    FIGURE 3
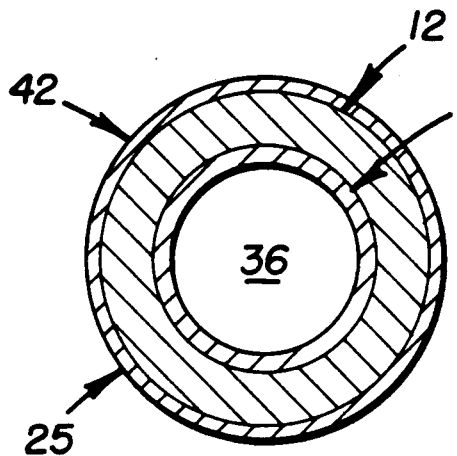
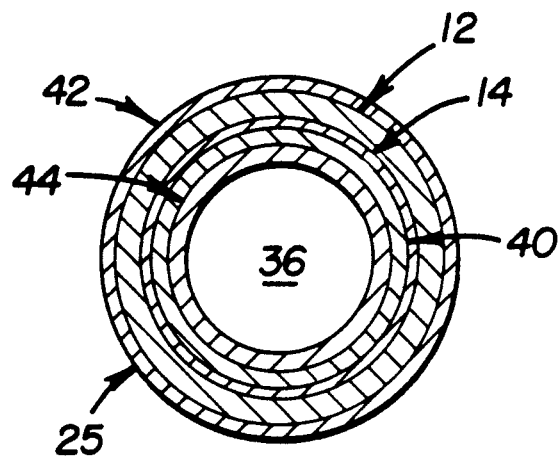
FIGURE 4    FIGURE 5
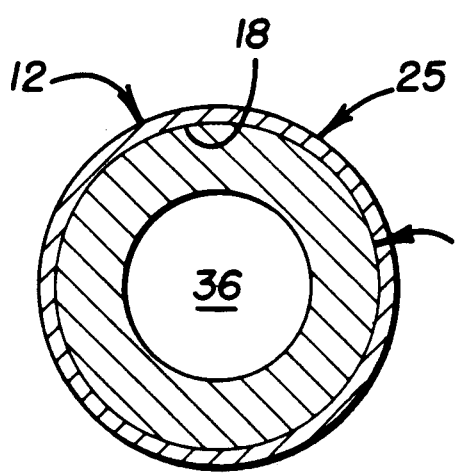
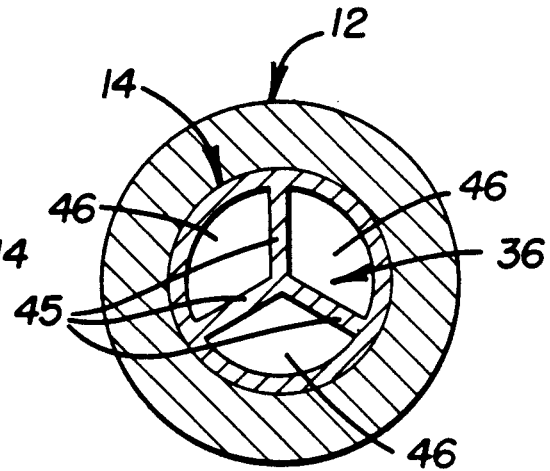
FIGURE 6    FIGURE 7

MULTI-LAYER CANNULA STRUCTURE

TECHNICAL FIELD

The present invention relates to a cannula structure useful for introducing or extracting fluids from a living test subject. More particularly, the invention relates to such a cannula structure which is made, at least partially, of a hydrophilic material which swells and usually softens when contacted with an aqueous liquid.

BACKGROUND OF THE INVENTION

Cannulas are regularly used to introduce and/or extract fluid from a living subject. For example, they are used as part of intravenous feeding and medicament introduction systems in hospitals and the like. They are also used to draw samples of blood for analysis from a patient.

One problem with the cannula structures of the prior art is that they have tended to become uncomfortable to the patient through irritation, particularly when maintained in place for relatively long periods of time. Recently this problem has been alleviated by utilizing a cannula material which swells, and generally softens, on insertion into the patient. Such swellable cannula can be inserted, for example via an over-the-needle technique, by making a relatively small puncture hole in a blood vessel and then withdrawing the needle. Thereafter, the cannula softens and swells providing an increased duct size for introduction and extraction of fluids.

Some such softenable and swellable cannula, for example, those disclosed in U.S Pat. Nos. 4,359,558; 4,424,305; 4,454,309 and 4,439,583, have certain problems of their own. In particular, due to softening the portion of such cannula exterior of the point of puncture of the patient the cannula can become more readily kinked Also, some hydrophilic materials, such as those cited above allow the migration of medicaments through the wall of the cannula and into contact with the puncture wound. This can lead to irritation whereby one of the main advantages of such softenable cannula, namely lack of irritation, can be lost.

It would also be desirable to be able to control the rate of hydration of swellable and/or softenable cannulae so as to assure that they can be fully inserted to a desired distance in the living subject before sufficient hydration occurs to cause enough softening to interfere with insertion of the cannula. This is true in instances wherein the cannula is of significant length and wherein several inches of the cannula may be fed into, for example, a blood vessel to position the end of the cannula in a desired location, for example in or near the heart.

The present invention is directed to overcoming one or more of the problems as set forth above.

DISCLOSURE OF INVENTION

In accordance with an embodiment of the present invention a cannula structure is set forth comprising a multilayer cannula structure having one or more layers comprising a hydrophilic material that increases in volume more than 1.3:1 upon contact with an aqueous medium at 37C. The hydrophilic layer comprises greater than 66% by area of the dry cross-sectional area of the wall of the cannula structure. One or more other layers are present. The other layer(s) are of a generally non-hydrophilic material bonded to at least one hydrophilic layer. The cannula structure swells greater than 20% in inner lumen cross-sectional area upon contact with an aqueous medium at 37° C. The non-hydrophilic material is such that the non-hydrophilic and hydrophilic layers remain bonded to one another following such swelling A cannula structure in accordance with the present invention has the advantage of retaining a desired amount of stiffness and a smaller diameter for proper insertion and positioning in a body but will hydrate, swell and generally soften after positioning thereby providing the benefits of being less traumatic and allowing greater flow and easier access for both extracting and injecting of fluids. Additionally the present invention provides the ability to control which areas of the cannula will soften and swell and to control the rate at which this softening and swelling takes place. The non-hydrophilic layer or layers can be made substantially water impermeable, selectively water permeable at a desired rate, substantially medicament impermeable, and/or medicament permeable at a desired rate. Accordingly, control is provided of where and/or how quickly the hydrophilic material may swell (and generally soften) and of the migration of medicaments into and out of the duct or lumen of the cannula. If the inner layer is substantially water impermeable that portion of the cannula which is not inserted into the living body does not become hydrated and therefore does not soften or swell wherein problems of kinking exterior of the body are alleviated.

BRIEF DESCRIPTION OF DRAWINGS

The invention will be better understood by reference to the figures of the drawings wherein like numbers denote like parts throughout and wherein:

FIG. 1 illustrates, in side and sections, a cannula structure in accordance with an embodiment of the present invention;

FIG. 2 illustrates the cannula structure of FIG. 1 taken along the line 2-2 shown therein;

FIG. 3 illustrates, in a view similar to FIG. 2, an alternate embodiment in accordance with the present invention;

FIG. 4 illustrates, in a view similar to FIG. 2, another alternate embodiment in accordance with the embodiment of the present invention;

FIG. 5 illustrates, in a view similar to FIG. 2, still another embodiment in accordance with the present invention;

FIG. 6 illustrates, in a view similar to FIG. 2, yet another embodiment in accordance with the present invention;

FIG. 7 illustrates, in a view similar to FIG. 2, another embodiment yet in accordance with the present invention;

FIG. 8 illustrates, in a view similar to FIG. 1, another embodiment still in accordance with the present invention; and FIG. 9 illustrates, in a partial enlarged view in side section, a detail in accordance with an embodiment of the present invention.

BEST MODE FOR CARRYING OUT INVENTION

In accordance with embodiments of the present invention shown in FIGS. 1 and 2 and in FIG. 6 a cannula structure 10 includes both a tubular outer layer 12 and a tubular inner layer 14. An outfacing surface 16 of the tubular inner layer 14 of FIG. 1 is bonded to a central bore 18 of the tubular outer layer 12 along its length, the central bore 18 proceeding from a distal end portion 20 to a proximal end portion 22 of the tubular outer layer 12.

Either the tubular outer layer 12 (FIGS. 1 and 2) or the tubular inner layer 14 (FIG. 6) is made of a hydrophilic material which swells and generally softens on being contacted with an aqueous liquid. The layer 12 or 14 which is not made of the hydrophilic material is made of a substantially non-hydrophilic material and is of a construction such that it yields sufficiently so that the central bore 18 of the outer layer 12 remains bonded to the outfacing surface 16 of the inner layer 14 as the hydrophilic material swells and generally softens. The tubular inner layer 14 has a central bore 24 through it via which fluid can be introduced or abstracted from a patient.

The total cross sectional area of the hydrophilic layer (12 or 14 in FIGS. 2 and 6) (or multiple layers as in some other embodiments) must, in accordance with the present invention, comprise at least about ⅔rds of the total cross-sectional area of the wall 25 of the cannula structure 10 and is preferably at least about ⅘ths of the total cross-sectional area of the wall 25. This relationship is essential to each of the embodiments of the invention. The hydrophilic material, in all embodiments of the present invention, must be such that it will swell in volume by a ratio greater than 1.3:1 upon contact with an aqueous medium, for example, on exposure to body fluids or tissue, at 37° C.

The one layer 12 or 14 (FIGS. 1 and 6) which is substantially non-hydrophilic must be sufficiently thin and yielding so that it will yield sufficiently to remain bonded to the other (hydrophilic) layer 12 or 14. It must not offer enough expansion resistance to the swelling expansion of the hydrophilic layer 12 or 14 to prevent the hydrophilic layer 12 or 14 from swelling sufficiently whereby the duct or lumen 36 of the cannula 10 increases in cross-sectional area by at least about 20% at 37° C., more preferably at least about 30%. When there is more than a single hydrophilic layer, and/or more than a single substantially non-hydrophilic layer, each non-hydrophilic layer must be sufficiently thin and yielding so that it yields sufficiently to remain bonded to the abutting hydrophilic layer or layers.

The substantially non-hydrophilic layer 12 or 14 must be selected from a material that when bonded to the hydrophilic layer 12 or 14 offers minimal resistance to the swelling expansion of the hydrophilic material and allows the internal lumen 36 of the composite cannula 10 to increase in cross-sectional area at least 20% and more preferably at least 30% at 37° C. Suitably, the substantially non-hydrophilic layer 12 or 14 has a softening ratio of at least 5:1 on being raised from room temperature (about 20° C.) to 37° C.

Considering the extremely low forces exerted by the swelling hydrophilic materials and the relatively large amount of swelling, it is surprising that the composite cannula structure 10 can be fabricated which will allow a composite structure to increase in lumen 36 as required above without separation of the hydrophilic layer 12 or 14 from the substantially non-hydrophilic layer 12 or 14 and will also offer the benefits associated with the substantially non-hydrophilic layer 12 or 14.

By selection of the materials for these two different types of layers and the design of the thicknesses and placement of these layers, cannula structures 10 with quite unusual properties can be fabricated. The design can control (1) where along its length such a composite cannula structure 10 will soften and swell, (2) the rate at which such a cannula structure 10 will soften and swell, and (3) the direction and rate at which medicaments can be delivered from the wall 25 of the composite cannula 10.

The hydrophilic layer 12 or 14 can be formulated from any hydrophilic material that when contacted with an aqueous medium at 37° C. will absorb sufficient fluids to swell in volume greater than 1.3:1. These materials also decrease in modulus (stiffness) along with swelling to provide a composite structure 10 that is relatively rigid for easy insertion and positioning into a living body but both softens to decrease the irritation to the body and increases the cross-sectional area of the lumen 36, thereby allowing greater access for extracting body fluids or delivering solutions and medications or for access of other devices.

The hydrophilic material of which either the outer layer 12 or the inner layer 14 is formulated can be virtually any hydrophilic material which has sufficient stiffness, when in the shape of the cannula structure 10, will allow easy insertion and/or guidance and positioning. In general, the cannula, if it is used in an over-the-needle type catheter and inserted through the skin, should, when non-hydrated and at room temperature, have a 2.5% Secant Modulus greater than about 20,000 N/cm$^2$ and preferably greater than about 28,000 N/cm$^2$ to prevent buckling or wrinkling upon insertion into the patient. The hydrophilic material must soften or exhibit a decreased 2.5% Secant Modulus on exposure to an aqueous liquid as when being inserted into the body of a patient. Particularly preferred compositions absorb aqueous liquid, i.e., hydrate, and therefore soften to a 2.5% Secant Modulus of less than 7,000 N/cm$^2$ when fully hydrated at 37° C. which reduces the trauma to the surrounding tissues of the patient. The term softening ratio is used herein to refer to the ratio of the 2.5% Secant Modulus values of the composition selected in the form of a tubular cannula initially (non-hydrated at room temperature) to the 2.5% Secant Modulus of the composition when softened (fully hydrated at 37° C.). At least a portion of the hydrophilic material composition must be hydrophilic. It is also preferred that the composition soften with a softening ratio of at least about 2:1.

Examples of swellable and softening polymers useful in the practice of the invention are those described in commonly assigned Co-pending Application Serial No. 780,543, filed Sept. 26, 1985, incorporated herein by reference. The preferred composition for the hydrophilic layer comprises:

(a) a first phase which comprises a substantially non-hydrophilic polymeric component; and (b) a second phase which comprises a hydrophilic polymeric component;

said material (i) being capable of absorbing water to an extent that its softens with a softening ratio of at least about 2:1 and swells with a swelling ratio of at least about 1.3:1; and (ii) when substantially completely hydrated at 37° C., having an energy to break of at least about 700 N-cm/cm$^3$ and a 2.5% Secant Modulus of less than about 7,000 N/cm$^2$.

Also useful are those swelling and softening polymers described in U.S. Pat. Nos. 4,359,558; 4,424,305; 4,454,309 and 4,439,583 of Tyndale Plains-Hunter Ltd. incorporated herein by reference.

The preferred hydrophilic layer composition essentially comprises a polyurethane diacrylate composition having from about 90 to about 65 weight percent of a hydrophilic polyurethane resin and from about 10 to about 35 weight percent of a diacrylate.

It is essential that the softening materials of the cannulae be such that they swell wherein at least a portion of the cannula inner cross-section of the duct (the lumen 36) increases to form an enlarged (by at least 20%) inner cross-section of the duct or lumen 36 when inserted in a living subject and maintained therein and/or when the duct 36 is contacted by an aqueous liquid for a period of time sufficient for the enlarged duct cross-section to form. Preferably, the duct cross-section increases from about 20% to about 400%.

The composition of the cannula may be partially cross-linked if desired. Cross-linking of the material selected for the cannula may also be used to adjust the 2.5% Secant Modulus of the composition to a desired value. Cross-linking may also increase the tensile energy to break of the material which has been softened. Cross-linking can also be used to control the delivery rates of medicaments in the composition.

Cross-linking can be effected by use of an appropriate cross-linking agent or by radiation, preferably in the presence of a cross-linking promoter, such as pentaerythritoltetraacrylate or the like. Or, the material can be cross-linked by high energy gamma or beta radiation.

The material of the cannula may contain additional ingredients such as stabilizers, antioxidents, radiopacifiers, medicaments, fillers or the like. For certain applications it may be advantageous to incorporate a water soluble or water dispersible medicament which can leach from the material when it contacts the fluids of the living subject. Such medicaments include anti-thrombogenic agents, antibiotics, antiviral agents, anticoagulants, anti-inflamatory agents, and the like.

The material of the substantially non-hydrophilic layer 12 or 14 is a polymeric material that absorbs less than 20% water at 37° C. and the term "substantially non-hydrophilic" as used herein indicates such a polymeric material. These polymeric materials preferably comprise thermoplastic materials that can be readily formed into these multilayer constructions. Of particular interest are the class of materials referred to as thermoplastic elastomers. These materials can be easily formed into the composite structures and possess sufficient elongation properties to allow the expansion of the cannula to take place upon hydration. Suitable thermoplastic elastomers include, for example, polyurethanes, polyamides, styrene/butadiene/styrene block copolymers, styrene/ethylene-butylene/styrene block copolymers, polyolefins, polyether or polyester block copolymers, polyether polyamide block copolymers, ethylene vinyl acrylates, ethylene propylene diene polymers and combinations of the above. Other useful materials include polyvinyl chloride and copolymers, polydimethyl siloxane polymers, acrylonitrile-butadiene-styrene block copolymers.

The substantially non-hydrophilic layer 12 or 14 can be selected to be a water barrier and/or a barrier to medicament diffusion so that it restricts the source of hydration for the hydrophilic layer 12 or 14 to only one surface. Examples of this are shown in FIGS. 2 and 6.

The substantially non-hydrophilic layer 12 or 14 can also be selected to control the rate at which aqueous solutions can transfer either into the inner hydrophilic layers as in FIGS. 4 and 5 or to control the rate at which medicants can diffuse from the hydrophilic layer 12 or 14 out of the composite structure 10.

The non-hydrophilic layer 12 or 14 may also be constructed so that it allows radial expansion of the cannula structure 10 but restricts the normal (axial) expansion of the hydrophilic layer 12 or 14. This provides the benefit of controlling and limiting the length expansion of a cannula that softens and swells in lumen cross-sectional area. This is extremely important when placing cannula into the vascular system especially when approaching the heart. The non-isotropic expansion properties can be achieved by one or more of several means. For example, the non-hydrophilic layer 12 or 14 can be reinforced with a fibrous filler such as glass or polymeric fibers 50 (FIG. 9) oriented in the axial direction of the cannula. Or, the non-hydrophilic layer 12 or 14 can be fabricated so that it is placed in axial tension (residual stress). Preferably, the lengthwise expansion of the cannula is restricted to be no more than 5% when the outer diameter of the cannula wall increases 15%.

Extremely useful non-hydrophilic materials are materials that will decrease in 2.5% Secant Modulus upon exposure to 37° C. and/or exposure to an aqueous medium. Of particular importance are those materials that will soften below 20,000 psi (2.5% Secant Modulus) or materials that decrease in 2.5% Secant Modulus more than 3:1.

A cannula selected such that it swells or softens should not do so appreciably during the time it is being inserted in a living subject or the like. It is preferable that such cannulae's swelling or softening time should be at least about 15 seconds and preferably at least about 60 seconds. The swelling of the cannula has several advantages. Swelling of the cannula permits insertion of a smaller device for equivalent fluid flow and/or can result in pressure around a wound site reducing bleeding and bacterial invasion into the wound and prevent catheter slip out, common causes for changing catheters prematurely. Increased cross-section of the cannula duct also permits increased flow through the cannula when compared with similar non-swelling cannula of identical initial dimensions. This allows access to smaller areas such as the veins in the limbs and easier insertion into the selected site. Cannulae which become soft are also advantageous. A soft cannula tends to cause less irritation to the intima (lining of the vein) and to the insertion site and is less likely to contribute to mechanical phlebitis. The softness of the cannula also permits it to float in a vein rather than lie on the point where inserted and consequently any infusion is delivered evenly helping to avert chemical phlebitis.

In the case where the cannula is used over a needle, the needle is selected having distal and proximal ends and having a sharpened insertion tip at the distal end. The needle may be selected to be either hollow or solid, that is, the term needle is used broadly to include hollow or solid longitudinal piercing members. The needle is positioned within the distal end portion of the longitudinal duct of the cannula with the insertion tip extending beyond the distal end of the cannula. An extraction wire, rod, etc., may optionally be attached to the proximal end of the needle and extend outward to the proximal end of the cannula. Extraction of the needle may be accomplished by pulling the needle or the extraction wire.

The catheter assembly of the invention is useful for inserting a cannula into a living subject. Preferably, the cannula is inserted in a blood vessel or cavity. The preferred use of the catheter assembly is for intravenous (IV) use. By living subject is meant any living thing, e.g., mammal, reptile, fish, etc., for which fluids are necessary to infuse or extract. In particular, the assembly is useful in mammals, specifically horses, cattle, dogs, cats and humans. The catheter assembly may be used, with or without an insertion needle, to infuse or extract liquids or to hook or connect to other apparatus or devices or can be used to position sensors or the like.

Referring to FIGS. 1 and 2, a cannula structure 10 in accordance with the present invention is illustrated. The proximal end portion 22 of the tubular outer and layers 12 and the proximal end portion 26 of the tubular inner and layers 14 are attached to a hub 28 by a hollow rivet 30. The distal end portion 20 of the tubular outer and layers 12 and the distal end portion 32 of the tubular inner and layers 14 are shaped into a tipped portion 34 of the cannula structure 10.

As will be seen in FIGS. 1 and 2 the outer hydrophilic layer 12 is significantly thicker (by at least a ratio of 2:1) than is the inner substantially non-hydrophilic layer 14. Thus, in accordance with the FIG. 1 and 2 embodiment the outer layer 12 is made of a hydrophilic material whereas the inner layer 14 is made of a substantialy non-hydrophilic material which yields sufficiently to remain bonded along its outfacing surface 16 to the bore 18 of the outer layer 12 as the hydrophilic material softens. Furthermore, the inner substantially non-hydrophilic layer 14 is of a construction such that it is either substantially water impermeable or allows water to pass through it at a relatively slow rate. Suitably, the rate of diffusion of water (or aqueous solution) through the substantially non-hydrophilic layer (14 in FIGS. 1 and 2) is less than ¼th the rate of diffusion through the hydrophilic layer (12 in FIGS. 1 and 2) even though the hydrophilic layer is thicker.

It should be noted that the inner layer 14 may either be made substantially water impermeable or may be made more slowly permeable to water than is the outer layer 12. Slow water permeability is desirable wherein the entire cannula 10 advantageously softens and swells whereas substantial water impermeability is desirable wherein it is desired to prevent the cannula structure 10 from softening and swelling due to an aqueous medium being in its central duct 36 but allowing such swelling where its out facing surface 16 is contacted by an aqueous medium, for example, body tissue.

FIG. 3 illustrates an embodiment of the present invention wherein a second hydrophilic tubular layer 40 is bonded to the bore 24 of the inner substantially non-hydrophilic layer 14. Note that the sum of the cross-sectional areas of hydrophilic layers 12 and 40 is at least ⅔rds of the total cross-sectional area of the wall 25. Such a construction is desirable when the medical profession wants to provide a first medicament which does contact the puncture wound, which puncture wound contacting medicament can be incorporated within the hydrophilic material of the outer layer 12 and can diffuse out of the material of the outer layer 12 into the surrounding tissue over a period of time. The inner layer 14 which serves to prevent medicament from migrating from the outer layer 12 into the lumen 36 then also serves to prevent migration of medicament which might be incorporated in the additional hydrophilic layer 40 (or which might be fluid passing through the central lumen or duct 36) into the tissue about the wound. In certain instances it is desirable to include a slowly releasing medicament in the additional hydrophilic layer 40, for example, an anti-thrombogenic material.

FIG. 4 illustrates an embodiment of the present invention having an additional thin substantially non-hydrophilic layer 42 which is bonded to an outwardly facing surface 38 of the outer layer 12. The thickness of the hydrophilic layer 12 is at least ⅔rds of the total crosssectional area of the wall 25. The additional thin layer 42 is of the same nature as is the tubular inner substantially layer 14. In the embodiment of FIG. 4 the rate of softening and swelling of the cannula structure 10 can be controlled by having the inner layer 14 and the additional thin layer 42 be such as to be slowly water permeable at a desired rate. The inner layer 14 and/or the additional thin layer 42 can also, if desired, control or prevent the diffusion of medicaments from the duct 36 to the surrounding tissue.

FIG. 5 illustrates an embodiment of the present invention which combines the features of the embodiments of FIGS. 3 and 4. In the embodiment of FIG. 5 there is an additional hydrophilic layer 40 (as in FIG. 3) and an additional thin substantially non-hydrophilic layer 42 as in FIG. 4. The additional layer 42 can control diffusion of water into the outer layer 12 from the surrounding tissue and can control diffusion of a medicament incorporated in the outer layer 12 outwardly to the surrounding tissue. The inner substantially non-hydrophilic layer 14 can serve as a barrier to diffusion of medicament in either direction across it. The additional hydrophilic layer 40 can have a medicament therein which is prevented from being diffusing outwardly by the inner layer 14 and which is allowed to diffuse inwardly at a controlled rate to the duct 36 through an additional substantially non-hydrophilic inner layer 44, of the same nature as the inner layer 14 of FIG. 2, and into the duct 36. In this manner the rate of introduction of a medicament, for example an anti-thrombogenic agent, to the duct 36 can be carefully controlled. At the same time a medicament such as an antibacterial agent can be allowed to diffuse out of the outer hydrophilic layer 12 at a controlled rate through the substantially non-hydrophilic layer 42.

FIG. 6 illustrates yet another embodiment of the present invention wherein the inner layer 14 is made of a hydrophilic material and is of the thickness and construction discussed with respect to the outer layer 12 for the embodiment of FIGS. 1 and 2. Also, in the embodiment of FIG. 6, the outer layer 12 is the thinner layer and is of the nature previously discussed with respect to the tubular inner layer 14 of the embodiments of FIGS. 1-2. The embodiment of FIG. 6 is useful in controlling the rate of softening and swelling (hydration) of the inner hydrophilic layer 14. The inner hydrophilic layer 14 could, for example, contain an anti-thrombogenic agent which slowly leachs into the duct 36. Contamination from the exterior environment through the thin substantially non-hydrophilic outer layer 12 of FIG. 6 into the hydrophilic inner layer 14 and therefrom into the duct 36, is alleviated.

FIG. 7 illustrates yet another embodiment of the present invention where separators 45 are located in the lumen 36 of the tubular section 14 to divide the lumen 36 into multiple channels 46. If desired, the separators 45 can be integral with the tubular section 14, as illustrated. This configuration has similar properties to those of the embodiment of FIG. 2 but allows separate flow of different solutions through the different channels 46 in either direction.

FIG. 8 illustrates an embodiment of the present invention similar to that of FIG. 1 but wherein the substantially non-hydrophilic tubular inner layer 14 does not extend the entire length of the cannula 10. Instead, the tubular inner layer 14 only extends slightly into the tissue 47 of the patient. The tip portion 34 of the cannula 10 does not have the substantially non-hydrophilic tubular inner layer 14. This allows the portion of the cannula structure 10 inserted into the tissue to soften and swell readily, while retaining non-swelling or very small swelling of the portion of the cannula 10 between the entry point into the patient's tissue 47 and the hub 28. Thus, this portion of the cannula 10 is in a rigid condition and is therefore highly kink resistant. In this situation the tubular inner layer 14 is generally substantially impermeable to migration of water.

Cannula structures 10 in accordance with the present invention have been made as follows:

Multilayer tubing as shown in FIGS. 1 and 2 has been fabricated by co-extruding the two materials 12 and 14 thorugh a laminer flow co-extrusion crosshead.

The non-hydrophilic material 14 was an aliphatic polyurethane thermoplastic (Tecoflex EG 60D, trademark of Thermedics, Inc.). It was extruded into the crosshead on a ¾" Waynne extruder using a 3:1 compression mixing screw.

The hydrophlic material 12 was a two phase blend of aliphatic thermoplastic urethane containing a radiopaque bismuth subcarbonate filler (Tecoflex 65D-B20, Trademark) and Polyethelene oxide (Polyox WSR 3154, Trademark). The components were preblended, extruded and pelletized. The pellets were then fed into a ¾" Brabender extruder and fed into the same co-extrusion crosshead as the non-hydrophilic material described above. More detailed descriptions of these materials can be found in co-pending patent application Ser. No. 780,543.

The resulting tubing was allowed to cool and then exposed to 5 megarads of electron beam radiation (beta).

The tubing was then tested by measuring its dimensions and physical properties in the non-hydrated state (23° C. and <50% relative humidity). The material was then hydrated in 37° C. water for a 24 hour period and retested for dimensions and physical properties. The table which follows summaries the results of this testing.

Industrial Applicability

The present invention provides a cannula structure 10 which swells and generally softens on being contacted with an aqueous medium and wherein the rate of swelling and softening can be controlled. The position along the cannula 10 at which the swelling and softening occurs can also be controlled. Medicament diffusion inwardly and outwardly from the cannula structure 10 can be controlled and/or prevented, as desired.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. A swelling multilayer cannula having proximal and distal end portions and a wall defining an inner lumen, comprising:
   (a) a hydrophilic layer structure having one or more hydrophilic layers having respective outer and inner surfaces and being formulated of a hydrophilic material characterized in that it increases in volume more than 1.3:1 upon contact with an aqueous medium at 37° C., said hydrophilic layer structure comprising at least ⅔rds of the cross-sectional area of said wall, said inner lumen swelling such that its cross-sectional area increases more than 20% upon contact of said hydrophilic layer structure with said aqueous medium at 37° C.; and
   (b) a substantially non-hydrophilic layer structure having one or more substantially non-hydrophilic layers having respective outer and inner surfaces and being formulated of a substantially non-hydrophilic material, an outer or inner surface of each of said hydrophilic layers being bonded to a corresponding inner or outer surface of at least one of said substantially non-hydrophilic layers, said bonded hydrophilic and substantially non-hydrophilic layers being of a construction such that they remain bonded to one another following swelling of said lumen such that its cross-sectional area increases more than 20% upon contact of said hydrophilic layer structure with said aqueous medium at 37° C.

2. A cannula as set forth in claim 1, wherein an innermost of said hydrophilic and substantially non-hydrophilic layers is a first of said substantially non-hydrophilic layers and defines said lumen and wherein a first of said hydrophilic layers has its inner surface bonded to the outer surface of said first substantially non-hydrophilic layer.

3. A cannula as set forth in claim 2, further including, in said lumen:
   at least one partition separating said lumen into at least two generally coextensive channels.

4. A cannula as set forth in claim 1, wherein said first substantially non-hydrophilic layer extends from a proximal end portion of said cannula but stops short of said distal end portion of said cannula.

5. A cannula as set forth in claim 1, wherein an innermost of said hydrophilic and substantially non-hydrophilic layer is a first of said hydrophilic layers and defines said lumen and wherein a first of said non-hydrophilic layers has its inner surface bonded to the outer surface of said first hydrophilic layer.

6. A cannula as set forth in claim 5, wherein said first substantially non-hydrophilic layer controls the diffusion rate of water or medicaments from said first hydrophilic layer to said outer surface of said first substantially non-hydrophilic layer.

7. A cannula as set forth in claim 1, wherein at least a first substantially non-hydrophilic layer of said substantially non-hydrophilic layer structure includes controlling means for controlling the lengthwise expansion of said cannula as it swells.

8. A cannula as set forth in claim 7, wherein said controlling means comprises a plurality of fibers oriented lengthwise and located in said first substantially non-hydrophilic layer.

9. A cannula as set forth in claim 7, wherein said controlling means comprises residual axial stress in said first substantially non-hydrophilic layer.

10. A cannula as set forth in claim 7, wherein said controlling means controls said lengthwise expansion to be no more than 5% when an outer diameter of said wall increases 15%.

11. A cannula as set forth in claim 1, wherein said one substantially non-hydrophilic layer is formulated of a thermoplastic material.

12. A cannula as set forth in claim 1, wherein said one substantially non-hydrophilic layer is formulated of a polyurethane material.

13. A cannula as set forth in claim 1, wherein said one substantially non-hydrophilic layer is formulated of an elastomeric material.

14. A cannula as set forth in claim 1, wherein said one substantially non-hydrophilic layer has a softening ratio of more than 5:1 on being raised from about 20° C. to 37° C.

15. A cannula as set forth in claim 1, wherein said one hydrophilic layer is formulated of a material having a 2.5% Secant modulus of less than 20,000 psi when hydrated at 37° C.

16. A cannula as set forth in claim 1, wherein said cannula decreases in 2.5% Secant modulus more than 10:1 upon exposure to an aqueous medium at 37° C.

17. A cannula as set forth in claim 1, wherein said hydrophilic layer material of said cannula comprises:
  (a) a first phase which comprises a substantially non-hydrophilic polymeric component; and
  (b) a second phase which comprises a hydrophilic polymeric component;
  said material (i) being capable of absorbing water to an extent that it softens with a softening ration of at least about 2:1 and/or swells with a swelling ratio of at least about 1.3:1; and (ii) when substantially completely hydrated at 37° C., having an energy to break of at least about 700 N-cm/cm$^3$ and a 2.5% Secant modulus of less than about 7,000 N/cm$^2$.

18. A cannula as set forth in claim 1, wherein said material, when at 37° C., has an energy to break of at least about 700 N-cm/cm$^3$ and a 2.5% Secant modulus of less than about 7,000 N/cm$^2$.

19. A swelling multilayer cannula having proximal and distal end portions and a wall defining an inner lumen, comprising:
  (a) a hydrophilic layer structure having one or more hydrophilic layers having respective outer and inner surfaces and being formulated of a hydrophilic material characterized in that it increases in volume more than 1.3:1 upon contact with an aqueous medium at 37° C., said hydrophilic layer structure comprising at least ⅔rds of the cross-sectional area of said wall, said inner lumen swelling such that its cross-sectional area increases more than 20% upon contact of said hydrophilic layer structure with said aqueous medium at 37° C.;
  (b) a substantially non-hydrophilic layer structure having one or more substantially non-hydrophilic layers having respective outer and inner surfaces and being formulated of a substantially non-hydrophilic material, an outer or inner surface of each of said hydrophilic layers being bonded to a corresponding inner or outer surface of at least one of said substantially non-hydrophilic layers, said bonded hydrophilic and substantially non-hydrophilic layers being of a construction such that they remain bonded to one another following swelling of said lumen such that its cross-sectional area increases more than 20% upon contact of said hydrophilic layer structure with said aqueous medium at 37° C.; and wherein an innermost of said hydrophilic and substantially non-hydrophilic layers is a first of said substantially hydrophilic layers and defines said lumen, wherein a first of said substantially non-hydrophilic layers has its inner surface bonded to the outer surface of said first substantially hydrophilic layer and wherein a second of said hydrophilic layers has its inner surface bonded to the outer surface of said first substantially non-hydrophilic layer.

20. A swelling multilayer cannula having proximal and distal end portions and a wall defining an inner lumen, comprising:
  (a) a hydrophilic layer structure having one or more hydrophilic layers having respective outer and inner surfaces and being formulated of a hydrophilic material characterized in that it increases in volume more than 1.3:1 upon contact with an aqueous medium at 37° C., said hydrophilic layer structure comprising at least ⅔rds of the crosssectional area of said wall, said inner lumen swelling such that its cross-sectional area increases more than 20% upon contact of said hydrophilic layer structure with said aqueous medium at 37° C.;
  (b) a substantially non-hydrophilic layer structure having one or more substantially non-hydrophilic layers having respective outer and inner surfaces and being formulated of a substantially non-hydrophilic material, an outer or inner surface of each of said hydrophilic layers being bonded to a corresponding inner or outer surface of at least one of said substantially non-hydrophilic layers, said bonded hydrophilic and substantially non-hydrophilic layers being of a construction such that they remain bonded to one another following swelling of said lumen such that its crosssectional area increases more than 20% upon contact of said hydrophilic layer structure with said aqueous medium at 37° C.;

an innermost of said hydrophilic and substantially non-hydrophilic layers being a first of said substantially non-hydrophilic layers and defining said lumen;

a first of said hydrophilic layers having its inner surface bonded to the outer surface of said first substantially non-hydrophilic layer; and wherein said substantially non-hydrophilic layer structure includes a second substantially non-hydrophilic layer having its inner surface bonded to the outer surface of said first hydrophilic layer.

21. A cannula as set forth in claim 20, wherein a second of said hydrophilic layers has its inner surface bonded to the outer surface of said second substantially non-hydrophilic layer and wherein said substantially non-hydrophilic layer structure includes a third substantially non-hydrophilic layer having its inner surface bonded to the outer surface of said second hydrophilic layer.

22. A cannula as set forth in claim 21, wherein said first substantially non-hydrophilic layer controls the diffusion rate of water or medicaments between said first hydrophilic layer and said lumen, said third substantially non-hydrophilic layer controls the diffusion rate of water or medicaments between said second hydrophilic layer and the outer surface of said third substantially non-hydrophilic layer, and said second substantially non-hydrophilic layer substantially prevents the diffusion of water or medicaments between said first and second hydrophilic layers.

23. A cannula as set forth in claim 20, wherein said first substantially non-hydrophilic layer controls the diffusion rate of water or medicaments between said first hydrophilic layer and said lumen and wherein said second substantially non-hydrophilic layer controls the diffusion rate of water or medicaments between said first hydrophilic layer and the outer surface of said second substantially non-hydrophilic layer.

* * * * *